United States Patent
Gunday et al.

(10) Patent No.: US 9,687,196 B2
(45) Date of Patent: Jun. 27, 2017

(54) ELECTRICALLY CONDUCTIVE BALLOON CATHETER

(75) Inventors: Erhan H. Gunday, Great Neck, NY (US); Lawrence J. Gerrans, San Anselmo, CA (US); Lon Chu, Pacifica, CA (US)

(73) Assignee: Sanovas, Inc., Sausalito, CA (US)

( * ) Notice: Subject to any disclaimer, the term of this patent is extended or adjusted under 35 U.S.C. 154(b) by 415 days.

(21) Appl. No.: 13/440,824

(22) Filed: Apr. 5, 2012

(65) Prior Publication Data

US 2012/0259193 A1    Oct. 11, 2012

Related U.S. Application Data

(60) Provisional application No. 61/472,950, filed on Apr. 7, 2011.

(51) Int. Cl.
  *A61B 5/107* (2006.01)
  *A61B 5/00* (2006.01)

(52) U.S. Cl.
  CPC .......... *A61B 5/6853* (2013.01); *A61B 5/1076* (2013.01); *A61B 2562/046* (2013.01); *F04C 2270/041* (2013.01); *Y10T 29/49124* (2015.01)

(58) Field of Classification Search
  CPC .......................... A61B 5/1076; A61B 5/6853
  USPC ....................................................... 600/587
  See application file for complete search history.

(56) References Cited

U.S. PATENT DOCUMENTS

| | | |
|---|---|---|
| 5,316,016 A | 5/1994 | Adams et al. |
| 5,653,684 A | 8/1997 | Laptewicz et al. |
| 5,752,522 A | 5/1998 | Murphy |
| 6,081,737 A | 6/2000 | Shah |
| 6,493,933 B1 | 12/2002 | Post et al. |
| 7,113,569 B2 | 9/2006 | Okumura et al. |
| 7,225,099 B1 | 5/2007 | O'Dwyer |
| 7,454,244 B2 | 11/2008 | Kassab et al. |
| 7,654,997 B2 | 2/2010 | Makower et al. |
| 7,722,538 B2 | 5/2010 | Khoury |
| 7,841,986 B2 | 11/2010 | He et al. |
| 2001/0051766 A1 | 12/2001 | Gazdzinski |
| 2002/0082681 A1 | 6/2002 | Boylan et al. |

(Continued)

FOREIGN PATENT DOCUMENTS

| | | |
|---|---|---|
| EP | 1913882 A1 | 4/2008 |
| WO | 9742871 A1 | 11/1997 |
| WO | 2004062525 A2 | 7/2004 |

OTHER PUBLICATIONS

T. K. Ghosh et al., Chaper 14 Formation of electrical circuits in textile structures, from Intelligent textiles and clothing edited by H. R. Mattila, 2006, Woodhead Publishing, pp. 239-282.*

(Continued)

*Primary Examiner* — Sean Dougherty
(74) *Attorney, Agent, or Firm* — St. Onge Steward Johnston & Reens LLC

(57) ABSTRACT

A balloon catheter having a mesh affixed thereto. The mesh is formed having members extending longitudinally and circumferentially about the balloon into columns and rows respectively. Each member of the mesh has a resistance or impedance that changes as the member is deformed such that, when the member comprises a length (L) a measured resistance or impedance will be different than when the member comprise a length ($L_1$) where $L_1$ is greater than L.

23 Claims, 12 Drawing Sheets

(56) References Cited

U.S. PATENT DOCUMENTS

| | | |
|---|---|---|
| 2003/0056599 A1 | 3/2003 | van Schoor et al. |
| 2006/0004353 A1 | 1/2006 | Koyfman et al. |
| 2007/0027667 A1 | 2/2007 | Osborn et al. |
| 2007/0219551 A1 | 9/2007 | Honour et al. |
| 2007/0299352 A1 | 12/2007 | Harlev et al. |
| 2008/0009746 A1 | 1/2008 | Forster et al. |
| 2008/0027358 A1 | 1/2008 | Gregersen et al. |
| 2008/0208174 A1 | 8/2008 | Johnson et al. |
| 2010/0087782 A1 | 4/2010 | Ghaffari et al. |
| 2010/0121270 A1 | 5/2010 | Gunday et al. |
| 2010/0210971 A1 | 8/2010 | Shabram |
| 2011/0010925 A1 | 1/2011 | Nix et al. |
| 2011/0034823 A1 | 2/2011 | Gelbart et al. |
| 2011/0034824 A1 | 2/2011 | Kassab |
| 2011/0034912 A1 | 2/2011 | de Graff et al. |

OTHER PUBLICATIONS

"Woven Electronic Textiles: An Enabling Technology for Healthcare Monitoring in Clothing" by Christoph Zysset et al., Sep. 29, 2010; pp. 1-4.
International Search Report and Written Opinion of the International Searching Authority; Application No. PCT/US2012/032747; Issued: Jul. 18, 2012; Mailing Date: Aug. 3, 2012; 8 pages.
International Search Report & Written Opinion of the International Searching Authority; Application No. PCT/US2012/032736; Issued: Jul. 22, 2012; Mailing Date: Aug. 3, 2012; 10 pages.
European Search Report Application No. EP 12 76 7259 Completed: Aug. 21, 2014; Mailing Date: Sep. 16, 2014 7 pages.
European Search Report Application No. 12 78 3026 Completed: Aug. 22, 2014; Mailing Date: Sep. 16, 2014 7 pages.

\* cited by examiner

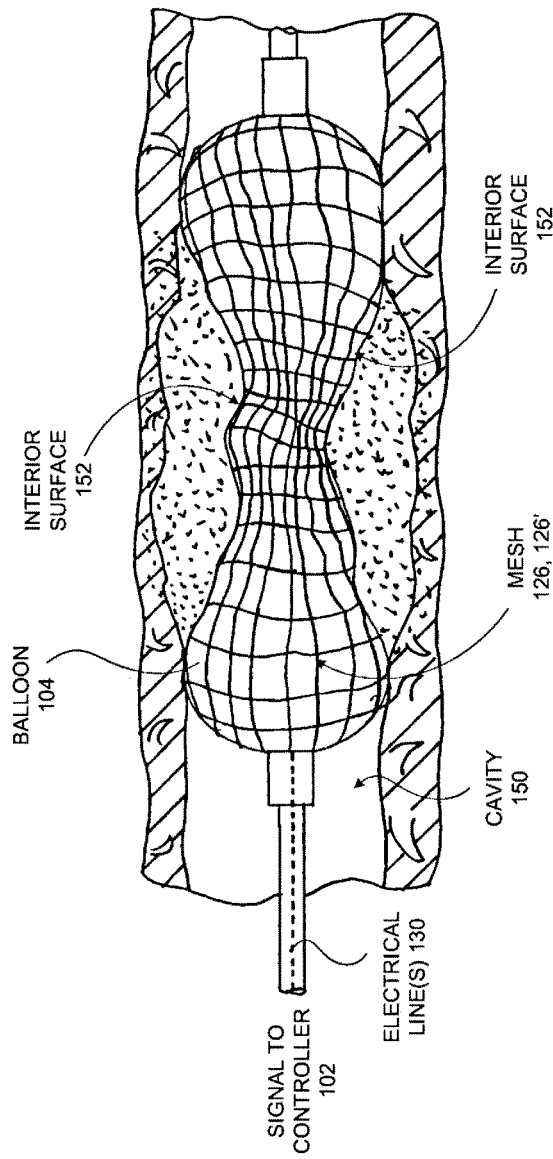

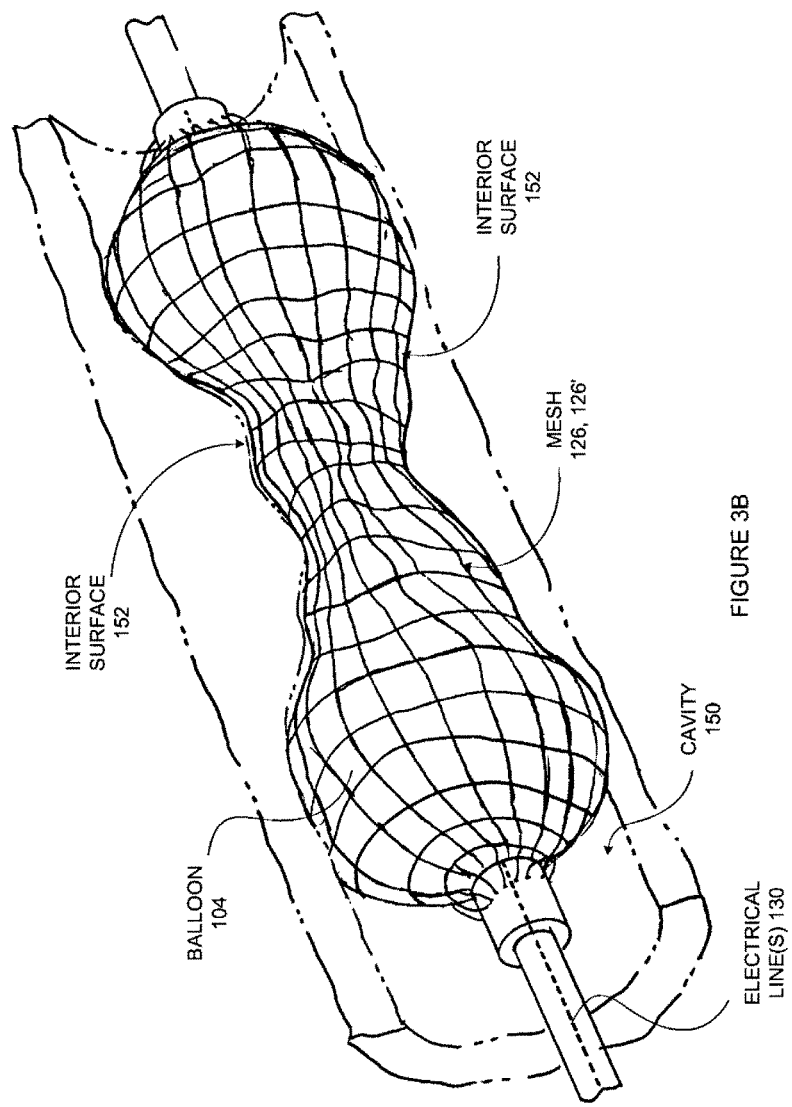

ELECTRICALLY CONDUCTIVE BALLOON CATHETER

CROSS-REFERENCE TO RELATED APPLICATIONS

The present application claims the benefit under 35 U.S.C. §119 (e) of the U.S. Provisional Patent Application Ser. No. 61/472,950 filed on Apr. 7, 2011, which is incorporated herein by reference.

FIELD OF THE INVENTION

The invention relates to a system and method for visualizing and measuring the interior of a body cavity and more specifically, relates to visualization and measurement of a body cavity with a balloon catheter by measuring the electrical characteristics of an inflated balloon in the body cavity.

BACKGROUND OF THE INVENTION

Balloon catheters are used for various medical procedures. For example, it is known to insert a balloon catheter into a passageway for dilation of the passageway such as is used in interventional bronchoscopy for the treatment of lung cancer and oft times, the resultant airway obstruction(s) that occur. Accordingly, balloon catheters have been routinely used with various endoscopes and with flexible and rigid bronchoscopes for dilation, as a tamponade to stop bleeding, and as an interference fixation device to hold instruments in place and prevent the retropulsion of those instruments under backflow pressure.

It is also known to use balloon catheters for removing undesirable biological material in bodily cavities. For example, inflatable balloon catheters may be employed as interventional tools for the excision and removal of unwanted materials—such as endoluminal obstructions and tumors and endovascular occlusions—in various applications, such as the interventional medical specialties of pulmonology, cardiology, urology, gynecology, gastro-enterology, neurology, otolaryngology, and general surgery. An example of such a device is disclosed in European Patent Application No. EP 1 913 882 by Karakoca. This device employs a balloon catheter with a hardening surface, which can be inserted into bodily cavities. After the device is inserted, the balloon is inflated, and the balloon is moved back and forth within the cavity such that the hardening surface resects on the unwanted biological material. For example, by pulling out the balloon, debris can be removed.

U.S. Patent Application Publication No. 2010/0121270 by Gunday (the '270 application) entitled Resector Balloon System, which is incorporated herein by reference, provides numerous improvements over Karakoca and relates to a balloon catheter with a textured surface that is operated in a pulsing fashion to shave the target material with minimal trauma. The '270 application discloses that a balloon system "is able to provide physiologic feedback to determine intra-lumen diameters." This is accomplished in one embodiment by the provision of "a sensor that determines the pressure of the fluid output to the balloon and a sensor that determines the flow of the fluid output to the balloon." Finally, the '270 application discloses that "by employing multiple, independently inflatable bladders or sinuses . . . one is able to more selectively and precisely . . . measure . . . intra-lumen diameters."

However, the '270 application teaches measuring intra-lumen diameters by means of measuring pressure and adjusting the pulsing of the balloon catheter for resecting accordingly. While this method is very effective for resecting target material with minimal trauma (e.g. pressure measurement coupled with the pulsing of the balloon catheter), it would be advantageous to utilize a balloon catheter to provide accurate rendering of the interior surface of the cavity. Accordingly, the pulsing of fluid into the balloon catheter as taught in the '270 application for resecting, along with the associated control system for controlling the pulsing of the pump, would not be needed for such an application.

Various imaging systems for visualizing internal structures are known, including, for example, Magnetic resonance imaging (MRI), nuclear magnetic resonance imaging (NMRI), or magnetic resonance tomography (MRT) and computed axial tomography (CAT) or sometimes shorten to computed tomography (CT) scan. While these methods can be very effective at visualizing internal structures, the cost associated with the purchase and use of these machines is relatively high.

In the field of orthopedics it is often difficult, if not impossible, to assess the spatial dynamics between articular surfaces; especially as the articular surfaces translate in opposition to one another throughout their ranges of motion. During arthroplasty procedures, in particular, it would be advantageous to understand the geometries of the articular surfaces as well as the spaces within the joint in the effort to perfect anatomic restoration and joint kinematics, in general.

It may also be advantageous to use an electrically conductive balloon catheter within the intramedullary canals of bones. The Orthopedic and Trauma science has long struggled to visualize and measure the inner surfaces of bones in real time. The inability to map bone anatomy has hindered surgeon's ability to appropriately size and implant arthroplasty implants (e.g.—Hip Replacement—Femoral and Acetabular Implants). It has also hindered surgeons ability to assess the displacement of fractures and to appropriately size and implant fracture management systems (e.g.—Tibial Rodding and Plating systems).

Intra-cavity mapping is also known, such as is disclosed in U.S. Pat. No. 7,654,997 (Makower et al.). However, while Makower et al. uses a catheter device, it requires the use of an external sensor (apart from the balloon) to map and provide a 3-dimensional view of the cavity. (See, Col. 40, I. 64—col. 41, I. 24; FIGS. 7D-7E). This is cumbersome, difficult to manipulate and not practical for relative small cavities (e.g., intravascular measurement).

U.S. Pat. No. 5,752,522 (Murphy) discloses an apparatus for determining cross-sectional dimensions of body lumens, such as the diameter of a blood vessel. (Abstract). However, while Murphy discloses a design that includes a catheter having conductor bands which vary in resistance with balloon circumference (col. 9, II. 13-15), Murphy is limited to disclosing "conductor bands." This will not provide a 3-dimensional view of the interior of a cavity, but rather, will only provide a cross-sectional circumference of a cavity. (See, FIG. 7).

What is desired, therefore, is a cost effective and reliable system and method for measuring and rendering internal structures of a body. It is further desired to provide a system and method for visualizing and measuring internal structures of a body that will not necessarily resect material from the internal structures during the processing of measuring the structures.

SUMMARY OF THE INVENTION

Accordingly, it is an object of the present invention to provide a balloon catheter system and method for visualizing and measuring internal structures of a body.

It is a further object of the present invention to provide a balloon catheter system and method for generating a three dimensional image of internal structures of a body and/or the spaces in between internal structures of the body.

It is yet another object of the present invention to provide a balloon catheter system and method for effectively visualizing internal structures in very small cavities (e.g., intravascular measurement).

It is a further object of the present invention to provide a balloon catheter system and method for effectively visualizing and measuring the spaces between and/or within internal structures in very small cavities (e.g., Intra-articular measurement; Intra-cavital measurement).

It is still another object of the present invention to provide a balloon catheter system and method for visualizing internal structures that provides a simple, cost-effective and reliable sensor(s) that generate a signal having a signal format that is robust and can be processed in a cost-effective manner.

It is also an object of the present invention to provide a balloon catheter system and method for visualizing internal structures in a body cavity that will not resect the internal structures.

These and other objectives are achieved, in one advantageous embodiment, by the provision of an electrically conductive mesh affixed to a balloon catheter. The balloon catheter may be inserted into the cavity to measure and provide a three-dimensional image of the interior of the cavity. As the balloon catheter is inflated and conforms to the inner surface area of the cavity, the electrically conductive mesh is stretched based on the inner surface area of the cavity. This stretching of the electrically conductive mesh (both in a lateral and a longitudinal direction relative to the cavity) will thereby cause a change in an electrical characteristic of the mesh (e.g., impedance or resistance) affixed to the balloon catheter. This change in electrical characteristic(s) may then be used to generate a three-dimensional rendering of the interior structure of the cavity.

It is understood that precise impedance measurement(s) are widely available and cost-effective. For example, to achieve high measurement accuracy with relatively low product cost, the signal processing technique of Discrete Fourier Transform (DFT) may be used with error correction to the impedance measurements. Software can effectively be used to control signal processing and error correction.

The mesh affixed to the surface of the balloon catheter may, for example, comprise a fiber mesh. It is contemplated that the mesh may be affixed to either the outer or inner surface of the balloon catheter. In either configuration, the balloon will expand to match the shape of the interior surface of the cavity.

The fiber mesh may comprise lycra, polyurethane, composite springs, or other appropriate material and will include electrical lines (or strings) therein that will vary in electrical characteristics depending upon the stretching or displacement of the mesh. In one example, when the electrical characteristic to be measured is impedance, as each portion of the mesh stretches outward to expand to the inner surface of the cavity the catheter balloon is to measure, the impedance of various portions of the mesh will change (e.g., the greater the stretching of the mesh the greater the change in impedance). In this manner, because the mesh includes portions that extend longitudinally and circumferentially about the balloon catheter, the device is able to provide a complete 3-dimensional view of the interior of the cavity as the system measures an impedance of each section of the mesh. Additionally, as no additional measurement device is needed apart from the balloon catheter itself, the device is particularly well suited for use in relatively small cavities (e.g., intravascular).

It is still further contemplated that the mesh may, in another embodiment, comprise a radio-opaque material such that, when inserted into a cavity and the balloon catheter is expanded, an external view of the expanded balloon catheter may be generated via an imaging device (e.g., the radio-opaque material will clearly show up on an external scan providing a detailed view of the current configuration of the catheter balloon. It is contemplated that both the electrical measurement of the mesh and imaging of the mesh having a radio-opaque material could be used to provide a high-resolution 3-dimensional rendering or imaging of the interior of the cavity.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, direction of data, modification of data, formatting and/or conversion of data, tagging or annotation of data, measurement, comparison and/or review of data, and may or may not comprise a program.

In one advantageous embodiment an imaging system for providing a 3-dimensional image of the interior of a cavity is provided comprising: a balloon catheter and a mesh affixed to the balloon catheter, the mesh having members extending longitudinally and circumferentially about the balloon catheter. The imaging system further comprises a controller coupled to the balloon catheter for controlling the inflation of the balloon catheter. The imaging system is provided such that each member of the mesh has at least one electrical characteristic that changes as the member is stretched such that, when the member comprises a length (L) a measured electrical characteristic will be different than when the member comprise a length ($L_1$) where $L_1$ is greater than L. The imaging system is further provided such that the controller measures the at least one electrical characteristic from each member and utilizes the measured electrical characteristics to generate a three-dimensional rendering of an interior surface of the cavity.

In another advantageous embodiment a balloon catheter is provided comprising a mesh affixed to a balloon. The mesh includes members extending longitudinally and circumferentially about the balloon into columns and rows respectively. Each member of the mesh has a resistance or impedance that changes as the member is deformed such that, when the member comprises a length (L) a measured resistance or impedance will be different than when the member comprise a length ($L_1$) where $L_1$ is greater than L.

In still another advantageous embodiment a method for constructing a balloon catheter is provided comprising the steps of forming a mesh by extending members longitudinally and circumferentially to form columns and rows. Each member of the mesh has a resistance or impedance that changes as the member is deformed. The mesh is provided such that when a member comprises a length (L) a measured resistance or impedance will be different than when the member comprise a length ($L_1$) where $L_1$ is greater than L. The method further comprises the step of affixing the mesh to a balloon.

Other objects of the invention and its particular features and advantages will become more apparent from consideration of the following drawings and accompanying detailed description.

BRIEF DESCRIPTION OF THE DRAWINGS

FIGS. 3A and 3B are illustrations of the balloon catheter of FIG. 2 inserted into a cavity for providing a 3-dimensional rendering of the cavity.

DETAILED DESCRIPTION OF THE INVENTION

Figure 1:
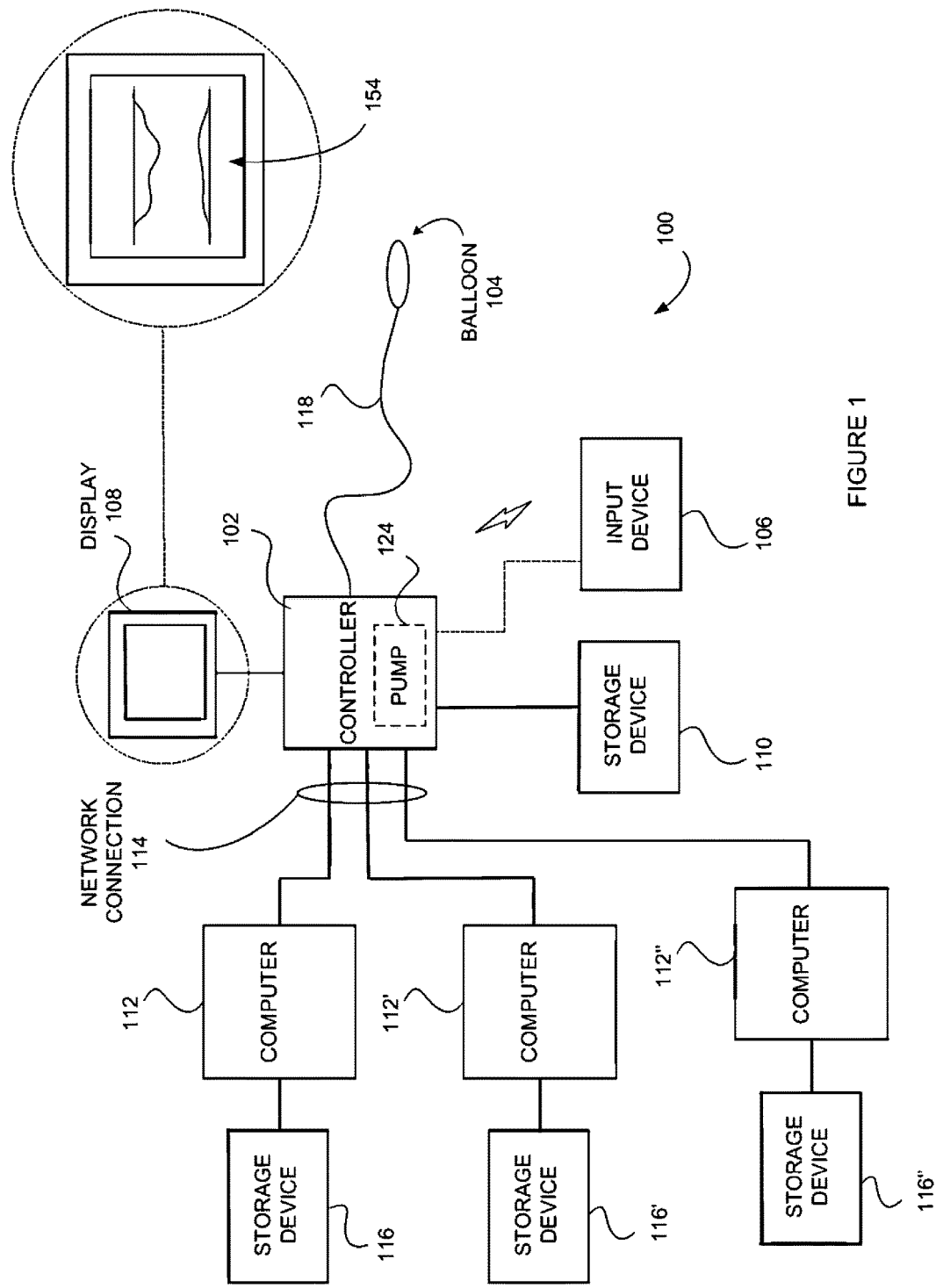
FIG. 1 is a block diagram on one advantageous embodiment of the present invention.

Referring now to the drawings, FIG. 1 is a block diagram of an advantageous embodiment of a system 100 for generating a three dimensional image of an interior of a body cavity 150 (FIGS. 3A and 3B).

The system 100 includes a controller 102, which may comprise any type of controller known in the art for controlling the inflating and deflating of a balloon 1104 attached thereto by means of a catheter 118 that includes electrical lines 130 to communicate with the controller 102. The controller 102 is coupled to an input device(s) 106 that may comprise virtually any type of interface including, for example but not limited to, a keyboard, a mouse, a touch screen or touch pad, a voice-activated control input device, etc. It is understood that input device 106 may be either wired or wireless, which is illustrated by the use of a dashed line and wireless transmission signal indication in FIG. 1. It is still further contemplated that the input device may comprise a mobile wireless device.

A display 108 is coupled to the controller that may present a visual rendering of the balloon catheter 104 in an inflated state, which may be stored on a storage device 110. A computer 112 (e.g., a personal computer) is also shown coupled to the controller 102 via a network connection 114. It is contemplated that the computer 112, 112', 112" may comprise a single computer or a network of computers (e.g., a plurality of hospital computers and associated storage devices, etc.), or a remote computer (e.g. in the doctor's office or an offsite location) where an image generated by the deformation of the balloon catheter 104 may be displayed and stored in a storage 116, 116', 116".

The rendering is a 3-dimensional rendering of the volume of the cavity. In one embodiment, the user may, by means of an input device, rotate the displayed 3-dimensional rendering to obtain different viewing angles. This allows, for example, the physician to get an extremely accurate view of the interior of the cavity. It may be desired to render the interior of the cavity, then, resect material from the cavity and generate a second rendering of the cavity after resection. This process could be performed in numerous stages. However, the system provides the ability to freely rotate the rendering allowing the user to view the volume surface of the cavity from virtually any viewing angle and magnification.

Figure 2:
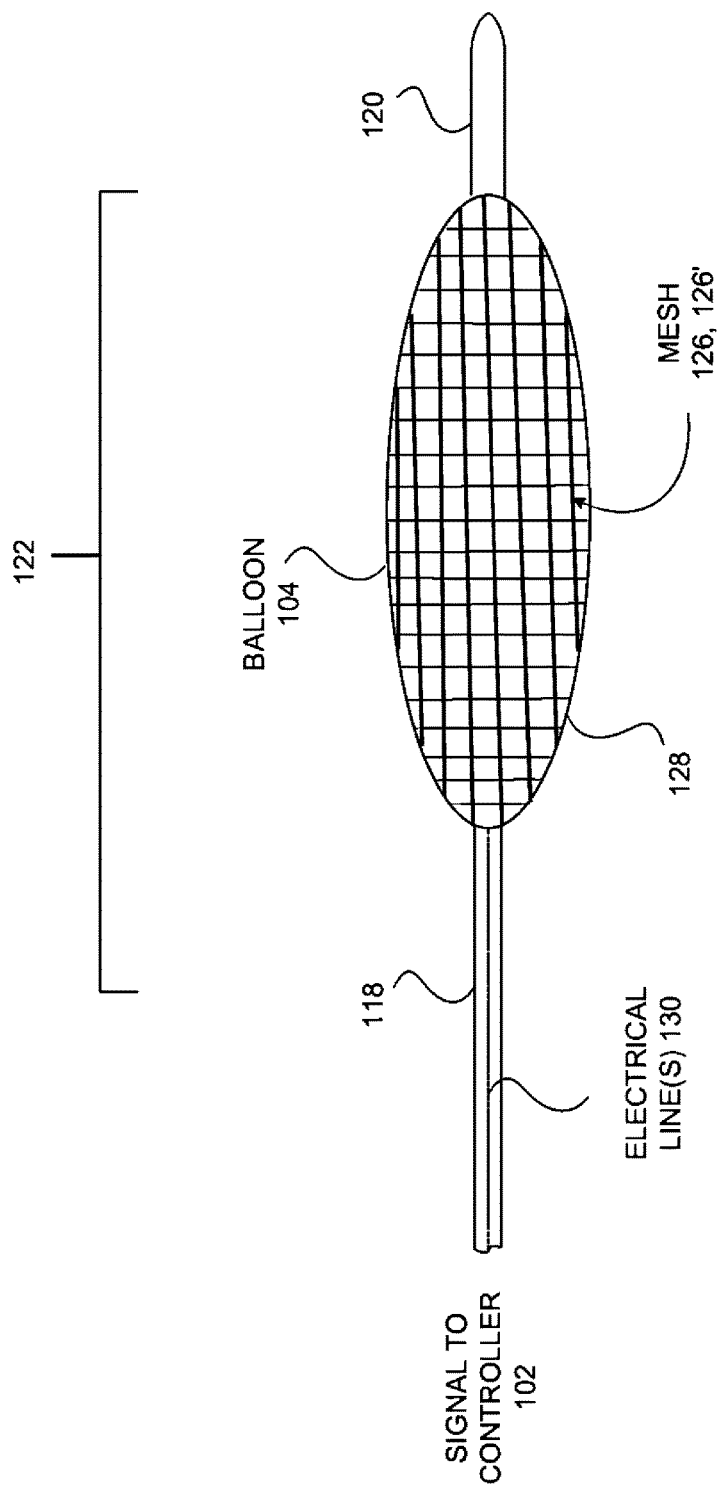
FIG. 2 is an illustration of the balloon catheter including the mesh according to FIG. 1.

Referring now to FIG. 2, the balloon 1104 connected to the controller 102 by means of the catheter 118 is shown in greater detail. The catheter 118, may comprise, for example, a polyethylene material and having an outer diameter of 0.5 mm-2 mm and a length of about 1.2 to 3 meters. The catheter is typically flexible such that it may be inserted into a cavity and may follow the course of the cavity freely without causing harm to the cavity (e.g., freely bendable to follow the course of the cavity, but non-compressible axially so that it may be inserted into the cavity). One example of an elongated body cavity would be insertion into the femoral artery in a patient's thigh, into which the catheter may be inserted to progress toward the patient's heart.

The catheter 118 may further include a bendable section 120 having a length of about 5 to 10 mm at the distal end of the catheter may serve as a safety tip. This is an advantageous feature because, when the catheter is inserted through the available opening of a bodily cavity, it will bend instead of puncturing the walls of the cavity.

A balloon 1104 may comprise a compliant material, such as latex, chronoprene, yulex, silicon, polyurethane, C-flex or any other suitable material and is typically positioned near a distal end 122 of the catheter 118 or at an otherwise desirable, predefined distance along the catheter 118. The balloon 1104 may come in a variety of lengths and diameters, which can be selected to suit the particular application for which the device is being used. Typically, such balloons 104 will have lengths selected from: 5 mm, 10 mm, 15 mm, 20 mm, 30 mm, 50 mm or greater. Such balloons 104 will also typically have diameters selected from: 2.5 mm, 5 mm, 10 mm, 15 mm, 20 mm, 30 mm or 50 mm or greater. This variety of available balloon sizes allows the balloon 104 to be used in bodily cavities of various diameters and dimensions, such as within articular joints (e.g., knee) or organs (e.g. Bladder) or within large and small bronchial branches, sinuses, and vessels, having different geometries and/or types of tumors and tissues to be treated. The controller 102 (which may include a pump 124, FIG. 1) supplies fluid (e.g. air, etc.) at a pressure ranging from approximately ½ atmosphere to approximately 6 atmospheres in order to be able to inflate the balloon 1104 to maximum size, ranging from 2.5 mml to 50 mml. It is understood that the pressure used to inflate the balloon will depend on the application. For example, rendering the interior of a bone cavity may require a higher inflation pressure than rendering the interior cavity of a blood vessel or artery. When soft tissue is rendered, the inflation pressure will be lower so as to avoid deforming the soft tissue.

In certain advantageous embodiments, the balloon 1104 may include imaging markers 126', such as radio opaque material or rings, located on the balloon 1104. Such markers can be selected and appropriately positioned in order to reflect the relevant waves of various imaging modalities (e.g., x-ray) in order to allow the use of such modalities to provide data so that the system is able to generate a 3-dimensional rendering of the interior of the cavity. It is understood that to generate a 3-dimensional rendering, a plurality of x-ray images from different views would have to be taken and assembled.

The balloon may also be covered with a fiber mesh 126 affixed to the surface 128 (either exterior or interior) of the balloon (or may be integral with the balloon). In certain advantageous embodiments, the surface 128 comprises a textured surface approximately 0.2 mm thick that is an integral part of the balloon 1104 and which is incorporated therein during the molding process. In these cases, the surface 128 is made by integrating into the balloon material a fine, fiber mesh 126, which can, in certain embodiments, comprise lycra, polyurethane, composite springs, or other appropriate material.

Referring now to FIGS. 3A and 3B, the balloon 1104 and catheter 118 is illustrated inserted into a cavity 150 and expanded to an interior surface 152 of the cavity 150. The mesh 126, 126' is provided such that upon stretching of the balloon 1104, the mesh 126, 126' is stretched to conform to the interior surface of the cavity 150. When the mesh 126' comprises a radio opaque material or rings, once inserted and inflated, an imaging device may be used to generate a 3-dimensional rendering of the interior of the cavity. For example, if the imaging device is an x-ray, the radio opaque material will reflect the x-ray wave lengths generating the 3-dimensional view of the interior surface of the cavity.

When the mesh 126 comprises a mesh having variable electrical characteristics (e.g., impedance or resistance), upon expansion of the mesh 126, the variable electrical characteristic(s) will change based on the extent that the mesh 126 stretches to conform to the interior surface 152. Accordingly, as shown in FIGS. 3A and 3B, the mesh will stretch more in some places (both longitudinally and circumferentially) and less in others. The controller 102 will monitor the electrical characteristic(s) change(s) in the mesh 126 and will generate an image 154 rendering of the interior surface of the cavity 150 based upon the change in the measured electrical characteristic(s) of the mesh 126.

It is further understood that an imaging device (not shown) may also be used to generate an image of the expanded balloon 1104, which could be used alone or in conjunction with the data generated by the changed electrical characteristic(s) to generate a 3-dimensional rendering of the interior surface 152 of the cavity 150.

Figure 4:
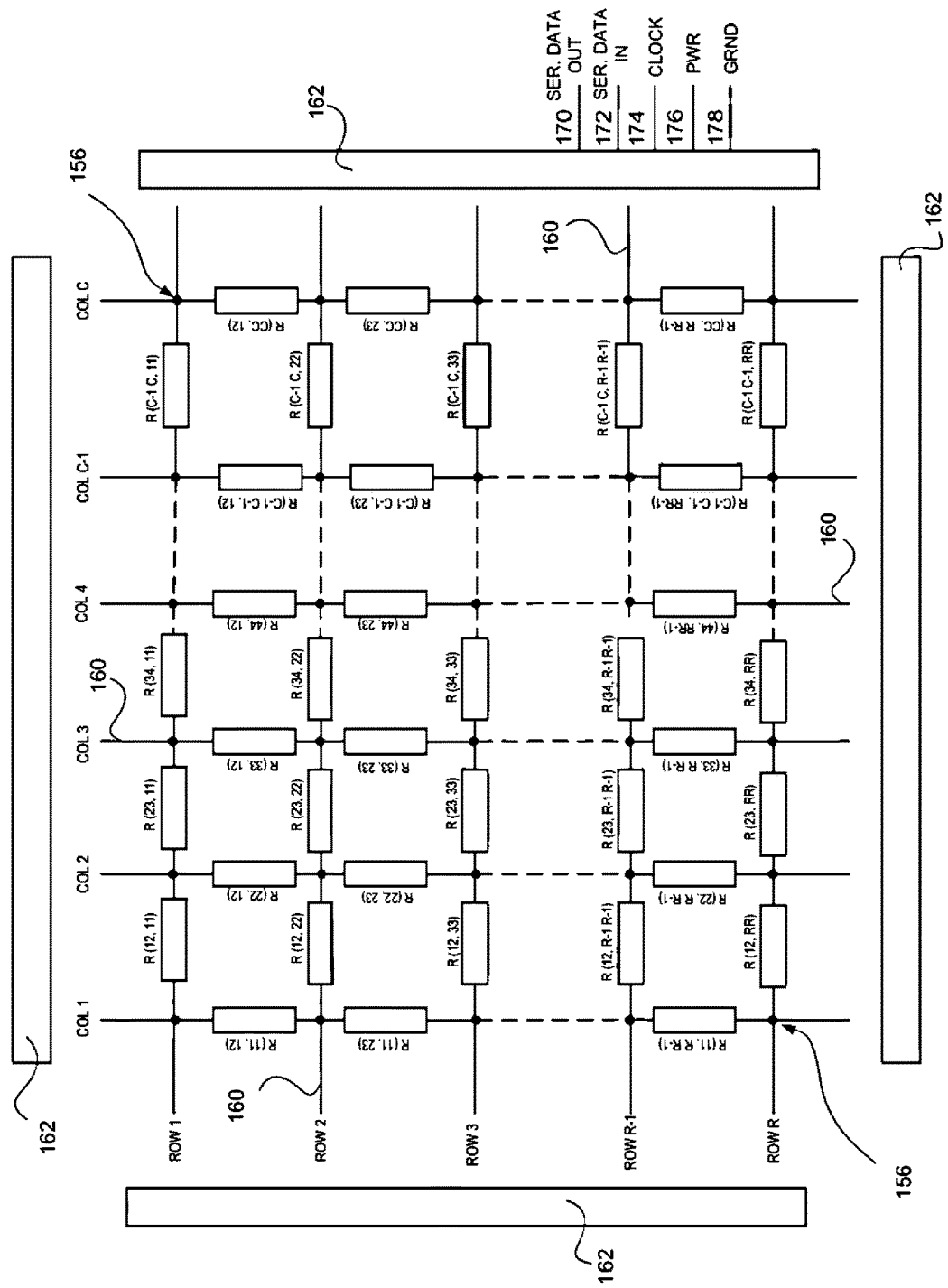
FIG. 4 is a representation of the mesh used in connection with the system of FIG. 1.

FIG. 4 represents the mesh made of elastic conductive material (elastic conductive yarn), which is on an inflated compliant balloon. The resistance of the mesh 126 changes as it is stretched. Thus the stretched material length is a function of its resistance. The function can be linear, exponential, logarithmic, or other. The resistance and change in resistance based upon specified deformation is based on the composition of material, including the amount of conductive fiber (i.e. iron) added thereto. The repeatable function is known in advance.

The rows of the conductive material are illustrated as running circumferential to the balloon 1104, while the Columns are the conductive material running lateral on the balloon104.

Also illustrated in FIG. 4, are resistances designated as Rn, which are shown illustrated as boxes representing each segment of conductive material as equivalent to a known resistance. The resistances are labeled according to the nodes 156 they are connected between. The electrical resistance value of each segment is a function of the amount that the conductive material segment has been stretched and thus the length of the segment.

Each node (represented by, for example, a dot) is a knot 158 (FIG. 7) where the conductive material may intersect. On an inflated balloon 104 (e.g., FIGS. 3A, 3B & 5), the nodes 156 are the only place where the conductive material touch each other and create a closed circuit between columns and rows when the balloon is inflated.

Elastic Conductive Yarns:

Elastic conductive yarns are available from various sources and can be manufactured in many different ways, including coating the elastic yarn with conductive material (polymers or metallics) or adding metal particles to the elastomers. In either case the electrical conductivity or the resistance of unit length of the yarn is a function of the amount of stretched. Resistance can be calculated from the following formula:

$$R = f(\Delta I) \qquad \text{Formula 1}$$

This function can be a linear, exponential, logarithmic, etc., but it is known and given the resistance of a segment of yarn, the length of that particular segment may be determined. For example, it is contemplated that a look-up table including the various resistance measurements and associated lengths may be provided in storage 110, 116, 116', 116". Once the resistance of a particular segment is determined, the actual resistance may be used to determine the length of the segment from the look-up table. Alternatively, the length may be calculated each time a resistance measurement is taken. An example of one method for generating an elastic conductive yarn can be seen from the article entitled Woven Electronic Textiles: An Enabling Technology for Healthcare Monitoring in Clothing by Christoph Zysset et al., Sep. 29, 2010.

Figure 7:
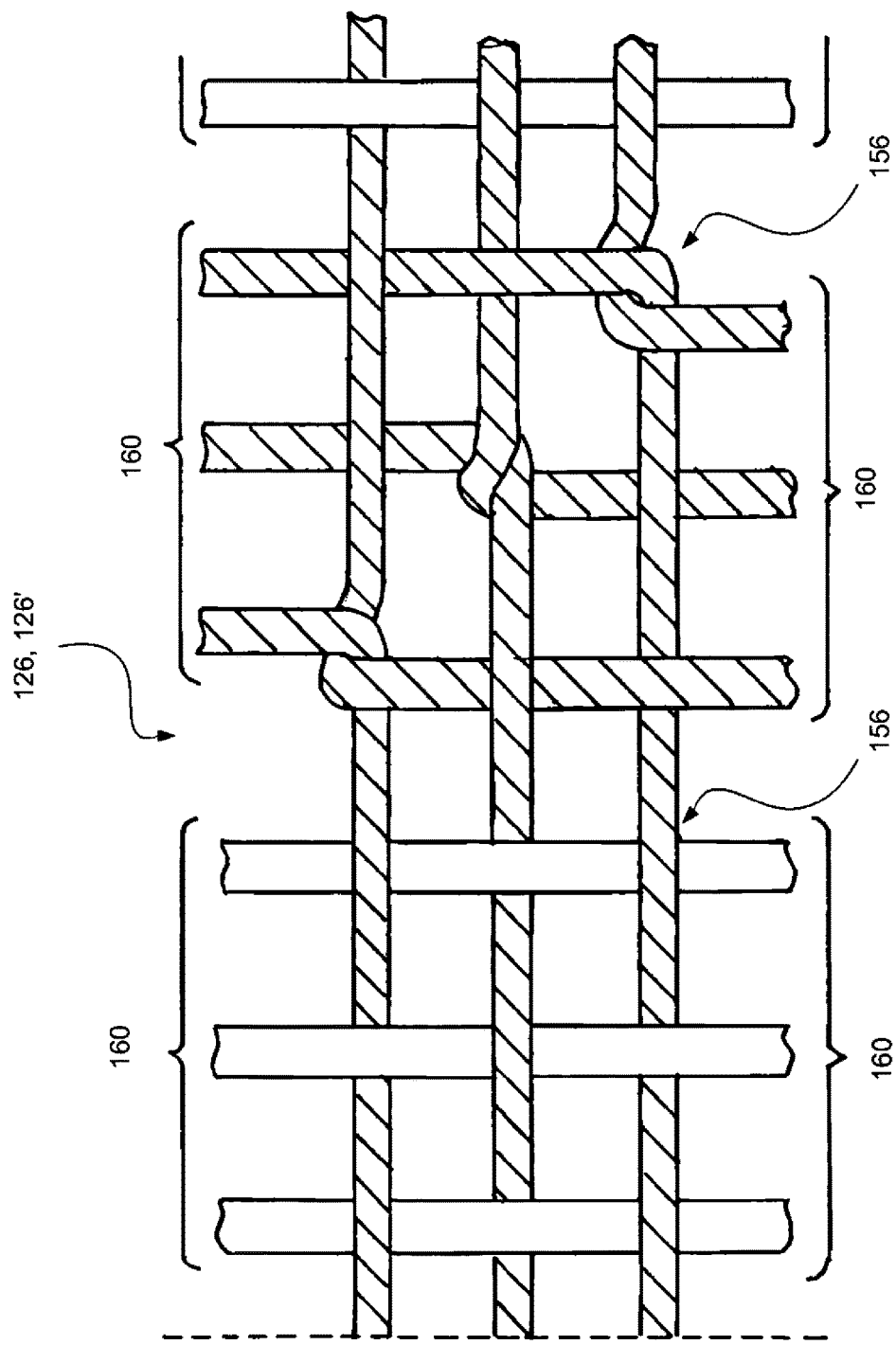
FIG. 7 is an illustration of one embodiment of the mesh construction according to FIG. 1.

Forming Balloon Sleeve Mesh From Conductive Yarn:

Many techniques can be used to produce the mesh 126 using conductive yarn similar to techniques used in textile manufacturing, including weft, warp circular or flat knitting as well as flat weaving creating a network of resistors. In case of flat techniques the yarn at two horizontal ends can be twisted and brought to the vertical top and bottom terminations. In FIG. 7 each end of the XY matrix that is formed is denote by X X' and Y Y'.

Figure 8:
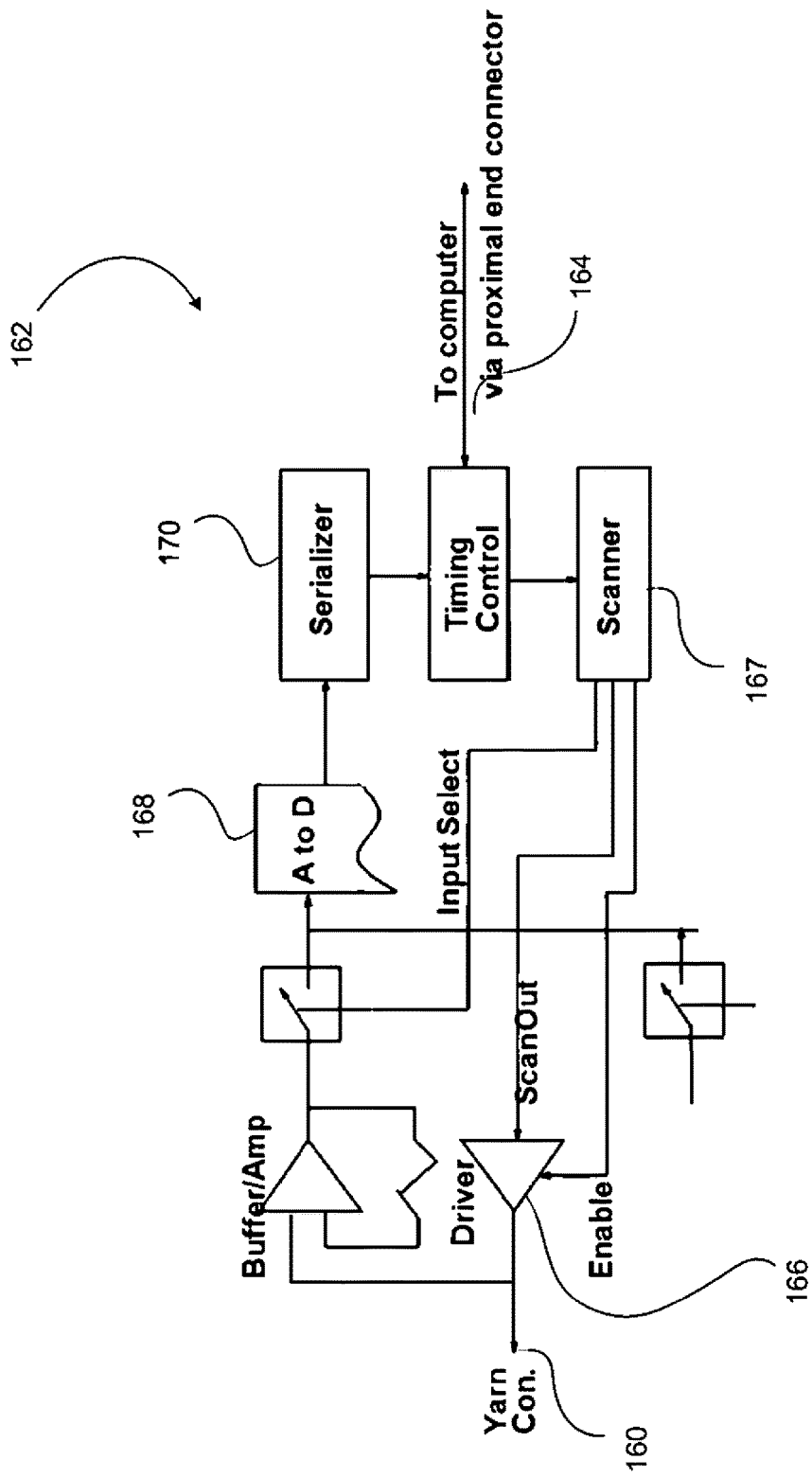
FIG. 8 is an integrated circuit block diagram according to the embodiment of FIG. 6.

Integrated Circuit:

Referring now to FIGS. 4 and 8, each end 160 of the elastic conductive yarn is connected to a pin of the integrated circuit 162. Each pin of the integrated circuit 162 is tri-state, such that it can be driven: 1) High: the pin is driven to high voltage (i.e. 5V), source current; 2) Low: the pin is driven to low voltage (i.e. 0V/Gnd), drains current; or 3) High impedance: the input impedance of the pin is at very high value, does not source or drain current).

There are integrated circuits 162 illustrated in FIG. 4. The integrated circuits 162 may include multiplexer(s) and de-multiplexer(s), which may be connected to a computer 112, 112', 112" via serial data in 170, serial data out 172, clock 174, power 176 and ground 178.

Figure 5:
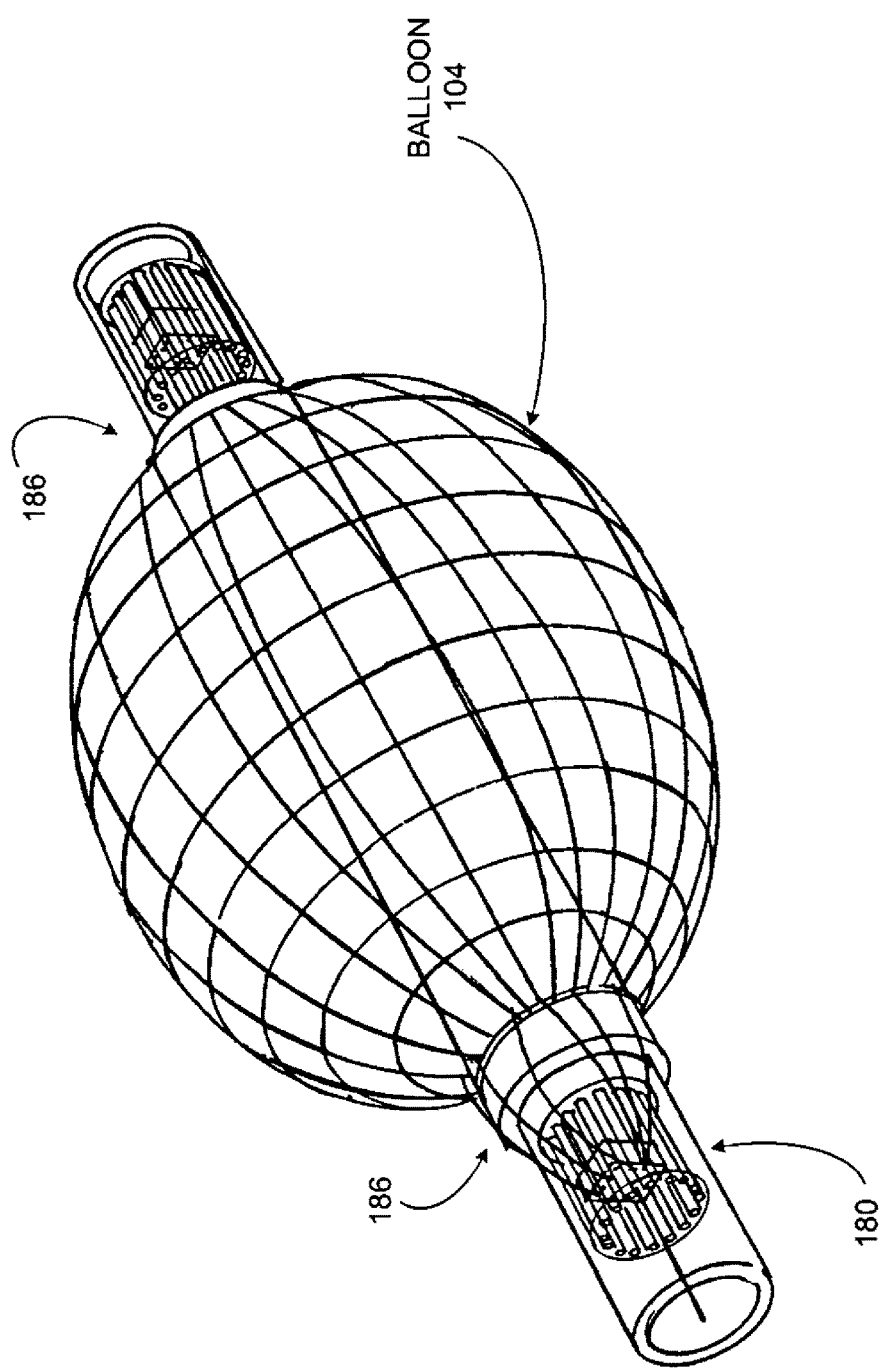
FIG. 5 is an illustration of the balloon and module according to the embodiment of FIG. 1.
Figure 6:
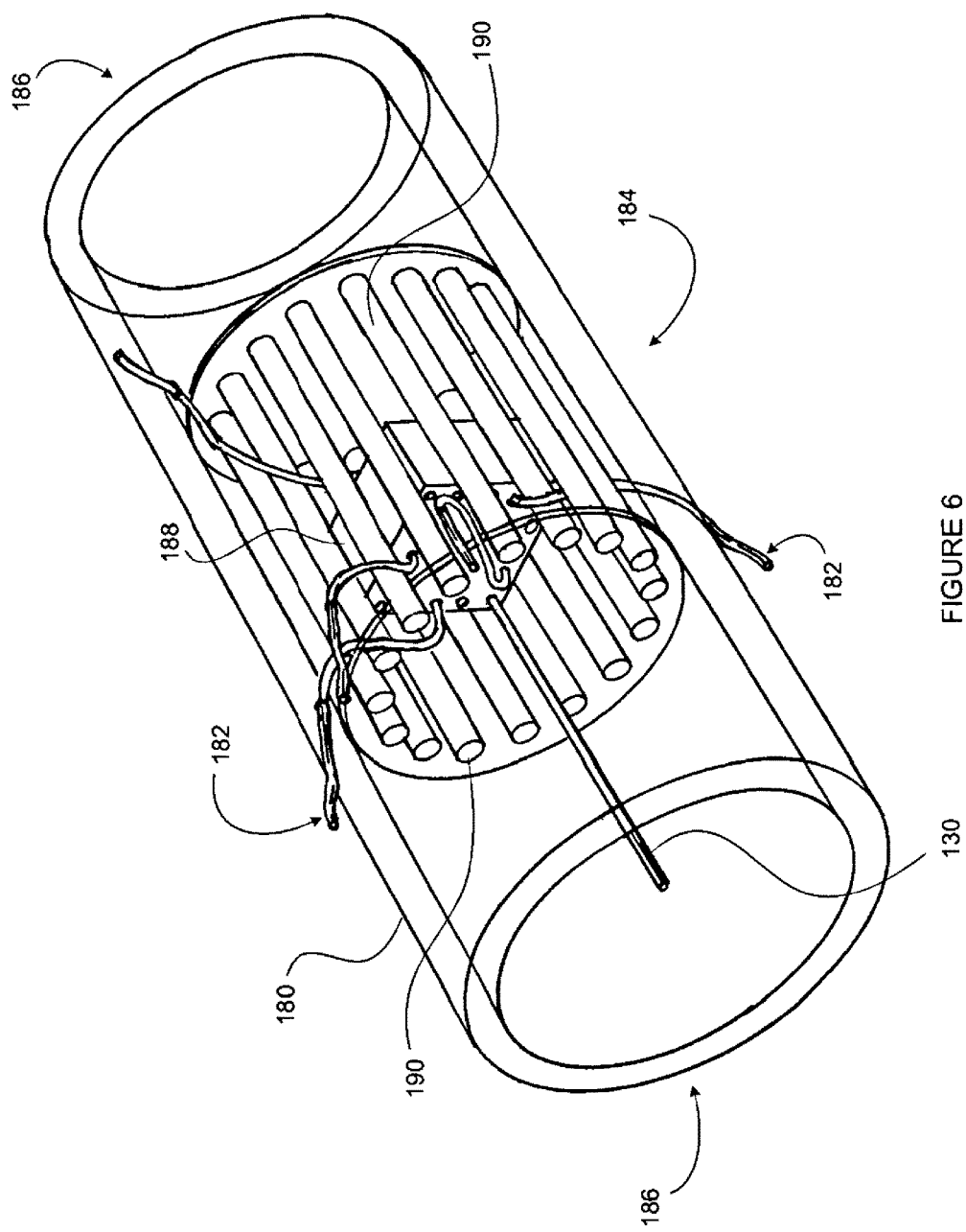
FIG. 6 is molded module an illustration of the module inserted into the tube according to the embodiment of FIG. 5.

The integrated circuit(s) 162 are provided as a very small package suitable to be mounted in a catheter tubing (FIGS. 5 & 6). It is contemplated that the elastic conductive yarn may, in an advantageous embodiment, be connected or coupled to integrated circuit(s) 162 with a conductive glue.

The timing controller 164 receives commands from a computer 112, 11', 112" via serial communication lines 166, 168 connected to the integrated circuit 162 at the proximal end. The timing controller 164 provides timing information for driver 166 and scanner 167.

Based on the data received a driver(s) 166 are enabled and the drive signal (High) is imposed to I/O pin(s), then all other pins are scanned and input to the analog to digital (ND) converter 168.

The digital output of the A/D converter 168 is input into a serializer 170 and sent to the computer 112, 112', 112" in a serial fashion.

Algorithms for Scanning the Mesh Resistor Networks:

Software controlling the drivers 166, may sequentially activate a single line of elastic conductive yarn while holding all other lines at high impedance. Each orthogonal line can, in one embodiment, then be scanned and the voltage measured can then be converted to a digital value.

It should be noted that, while various functions and methods have been described and presented in a sequence of steps, the sequence has been provided merely as an illustration of one advantageous embodiment, and that it is not necessary to perform these functions in the specific order illustrated. It is further contemplated that any of these steps may be moved and/or combined relative to any of the other steps. In addition, it is still further contemplated that it may be advantageous, depending upon the application, to utilize all or any portion of the functions described herein.

For example, when Col. 1 is driven the equivalent circuit for Row R is:

$$R(12,RR)+R(23,RR)+R(34,RR)+ \ldots +R(C\text{-}1\ C\text{-}1, RR) \quad \text{(Equation 1)}$$

When Col. 1 is driven the equivalent circuit for Row R-1 is:

$$R(11,R\ R\text{-}1)+R(12,R\text{-}1\ R\text{-}1)+R(23,\ R\text{-}1\ R\text{-}1)+ \ldots +R(C\text{-}1\ C,R\text{-}1\ R\text{-}1) \quad \text{(Equation 2)}$$

And so on.

When Col. 2 is driven the equivalent circuit for Row R is:

$$R(23,RR)+R(34,RR)+ \ldots +R(C\text{-}1\ C\text{-}1,RR) \quad \text{(Equation 3)}$$

When Col. 2 is driven the equivalent circuit for Row R-1 is:

$$R(22,R\ R\text{-}1)+R(23,\ R\text{-}1\ R\text{-}1)+ \ldots +R(C\text{-}1\ C,R\text{-}1\ R\text{-}1) \quad \text{(Equation 4)}$$

And so on.

The value of resistor R(12,RR) will be the difference between the equations 1 and 2. Similarly, R(12, R-1 R-1)+R(11, R R-1) will be the difference between the equations 3 and 4.

When scanning is done with the second set of ICs horizontal R(12, R-1 R-1)+R(11, R R-1) is resolved and each resistor value is known (FIG. 4).

It is understood that there are a number of different methods that the mesh resistor network may be scanned to determine or approximate the resistance of each segment. Some of these methods include: utilization of Kirchoff's laws, elimination of segment, transfer matrix, Green's function resistance distance, etc.

Surface Mapping

The following symbols are used for surface mapping (x, y, t): a (x, y) grid at time t R(x, y, t): a measured resistor value at time t G(x, y, t): four R value measured within a grid at time t Diff(x, y, t): G value difference between time t and t−1

T(x, y, t): a transformation matrix derived from G(x, y, t)

T'(x, y, t): error corrected transformation matrix from T

G'(x, y, t): projected G value from T'(x, y, t−1)

E(x, y, t): difference between G and G' at time t

Figure 11:
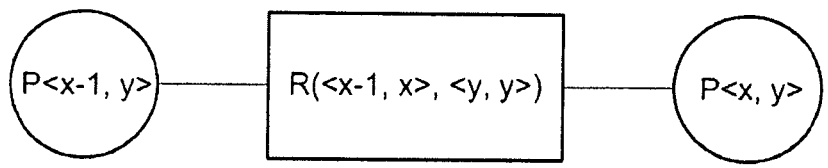
FIG. 11 is a schematic representing variables used for surface mapping.
Figure 12:
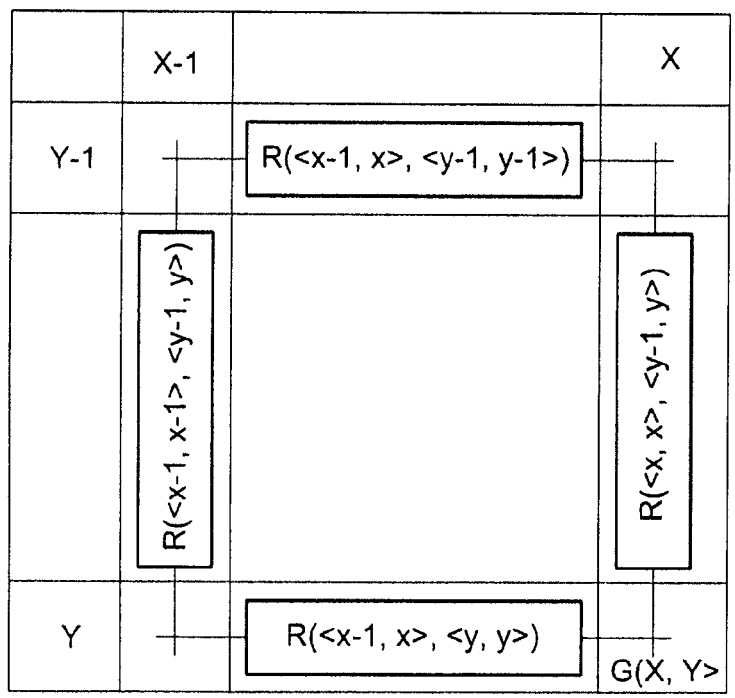
FIG. 12 is a schematic representing variables used for surface mapping.

Referring to FIG. 11, let R(<x−1 x>, <y, y>) denotes measured resister value between point <x−1,y> and point <x, y>.

Referring to FIG. 11, G(x,y) denotes four resistors value measured among point <x−1, y−1>, point <x−1, y>, point <x, y−1>and point <x, y>.

$$G(x,\ y)=\{R(<x\text{-}1,\ x\text{-}1>,\ <y\text{-}1,\ y>),\ R(<x\text{-}1,\ x>,<y\text{-}1,\ y\text{-}1>),\ R(<x\text{-}1,x>,\ <y,\ y>),\ R(<x,\ x>,<y\text{-}1,\ y>)\} \quad \text{(Equation 5)}$$

Let G(x, y, t) denotes as G(x, y) measured at the time t. Let Diff(x, y, t) denotes as resisters value difference between G(x, y, t) and G(x, y, t−1).

$$\text{Diff}(x,\ y,\ t)=SQRT((G(x,\ y,\ t)\text{-}G(x,\ y,\ t\text{-}1))*2) \quad \text{(Equation 6)}$$

Let T(x, y, t) denotes a 5×5 transformation matrix between G(x, y, t) and G(x, y, t−1).

$$G(x,\ y,\ t)=G(x,\ y,\ t\text{-}1)*T(x,\ y,\ t) \quad \text{(Equation 7)}$$

Both G(x, y, t) and G(x, y, t−1) are known values.

$$\text{INVERSE}(G(x,\ y,\ t\text{-}1))*G(x,\ y,\ t)=\text{INVERSE}(G(x,\ y,\ t\text{-}1))*G(x,\ y,\ t\text{-}1)*T(x,\ y,\ t) \quad \text{(Equation 8)}$$

$$\text{INVERSE}(G(x,\ y,\ t\text{-}1))*G(x,\ y,\ t)=I*T(x,\ y,\ t) \quad \text{(Equation 9)}$$

$$T(x,\ y,\ t)=\text{INVERSE}(G(x,\ y,\ t\text{-}1))*G(x,\ y,\ t) \quad \text{(Equation 10)}$$

Surface Mapping Algorithm.

1. At t=t0 a. save all G(x, y, t0) for [x=1 ... m] and [y=1 ... n]

2. From t=t1 to to a. for each G(x, y, t)

i. Compute Diff(x, y, t);

ii. Save the x and y location for the smallest Diff(x, y, t) value to X and Y;

iii. Use Simple Value Decomposition (SVD) algorithm or to solve T(x, y t) from:

G(x−2, y−2, t) G(x−1, y−2, t) G(x, y−2, t) G(x+1, y−2, t) G(x+2, y−2, t)

G(x−2, y−1, t) G(x−1, y−1, t) G(x, y−2, t) G(x+1, y−2, t) G(x+2, y−2, t)

G(x−2, y, t) G(x−1, y, t) G(x, y, t) G(x+1, y, t) G(x+2, y, t)

G(x−2, y+1, t) G(x−1, y+1, t) G(x, y+1, t) G(x+1, y+1, t) G(x+2, y+1, t)

G(x−2, y+2, t) G(x−1, y+2, t) G(x, y+2, t) G(x+1, y+2, t) G(x+2, y+2, t)

iv. If (t>t1)
  1. Compute the projected G'(x, y, t) using T'(x, y, t−1);
  2. Compute the difference between G(x y, t) and G'(x, y, t) as E(x, y, t);
  3. Use Least Square Model Fitting(LSM) algorithm to fit the E(x, y, t) within [x−9 . . . x+9, y−9 . . . y+9] mesh grids.

3. At t=t3 to tn
 a. Using G(x, y, t−1) and T'(x, y, t−1) and E(x, y, t−1) to plot the 3D surface as:

G(x, y, t)=G(x, y, t−1)*T'(x, y, t−1)+E(x, y, t−1) at the view port.

This is the equation that is used for generating the rendering from different viewing angles.

Flexible Electronic Circuitry and Method of Connecting to Conductive yarn:

Methods of making flexible electronics 184 (including integrated circuit 162) suitable for interface with textiles, yarn and treads are available. One such method is disclosed in patent U.S. Pat. No. 6,493,933.

FIGS. 5 & 6 show one method of molding such electronics 184 inside a tubing 180 such that the flexible connection leads 182 extended to the outside of the tubing 180.

Each end 186 of the tubing 180 is then inserted into the catheter tubing before and after the balloon 1104 with the mesh sleeve.

It should be noted that the molded structure 188 that the integrated electronic circuit 184 is mounted in has holes 190 such that the balloon inflation medium can pass through.

These flexible connection leads 182 expand and contract as the balloon 1104 is inflated and deflated.

The desired elastic yarn member (mesh 126) is attached to the leads 182 by various methods, including stitching, gluing (conductive), mechanical coupling (folding, squeezing, etc.) or combinations thereof.

Figure 9:
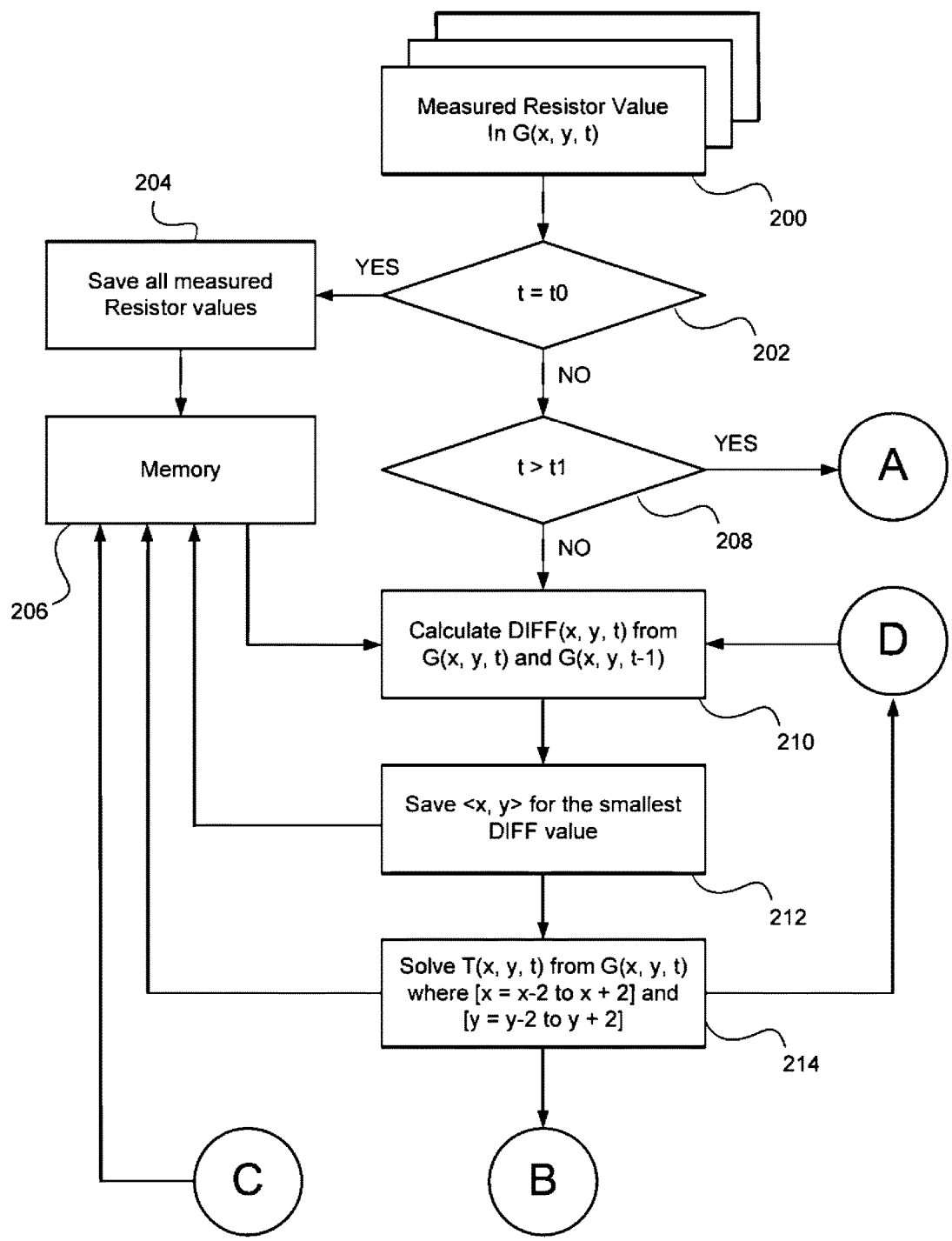
FIG. 9 is a flow diagram of a method according to the embodiment of FIG. 1.
Figure 10:
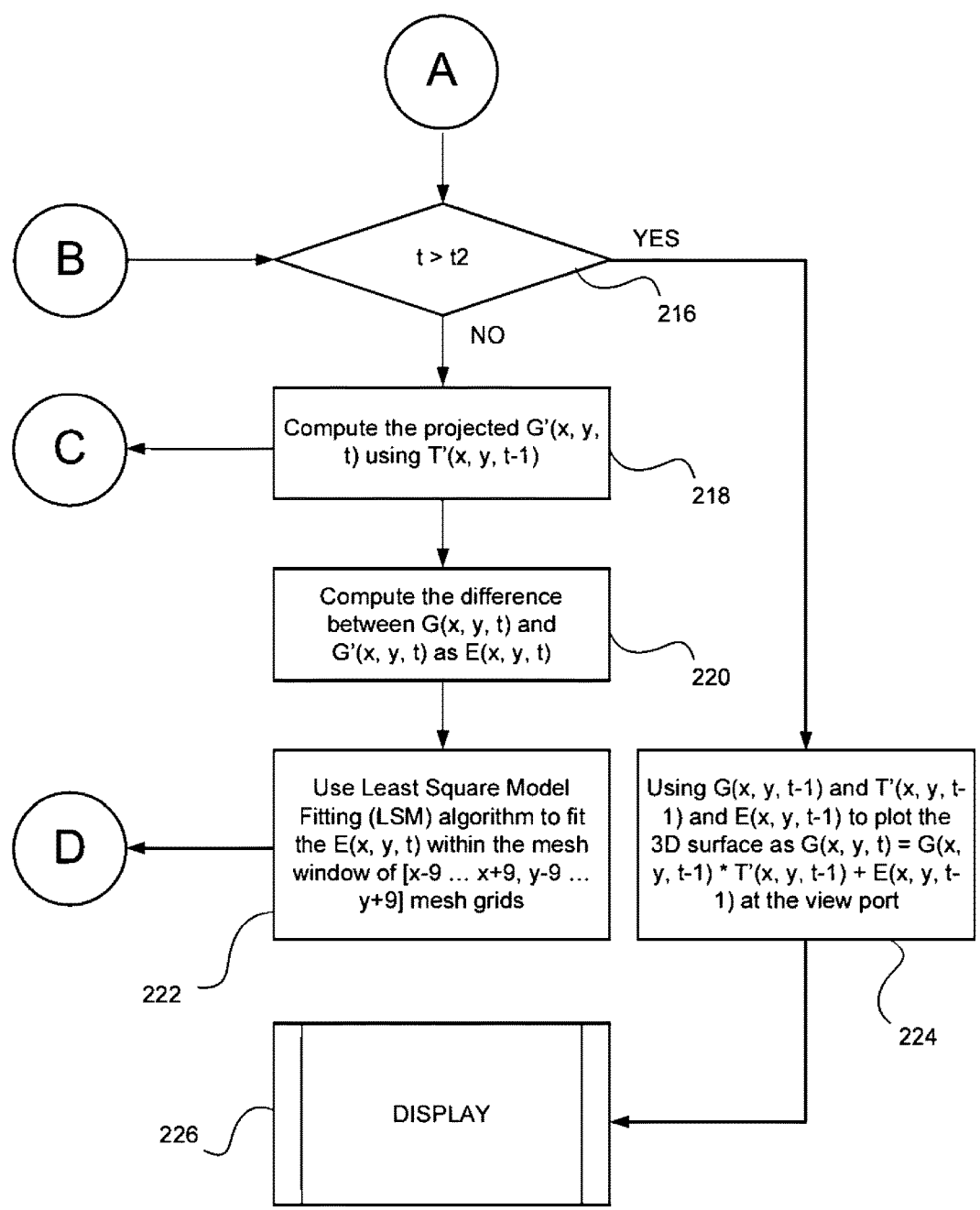
FIG. 10 is a continuation of the flow diagram according to FIG. 9.

FIGS. 9 and 10 are a flow diagram illustrating a method for generating a three dimensional rendering of a cavity by measurement of resistor values. At step 200, the system measures resistor values in G(x, y, t) and proceeds to step 202 to determine if t=0. If t=0, then the system saves all measured resistor values 204 in memory 206. If t≠0, the system determines if t>t1 at step 208. If t≠t1, then the system calculates the DIFF(x, y, t) from G(x, y, t) and G(x, y, t−1) at step 210, and saves <x, y> for the smallest DIFF value at step 212 in memory 206. The system then proceeds to solve T(x, y, t) from G(x, y, t) where [x=x−2 to x+2] and [y=y−2 to y+2] at step 214, which is also saved in memory 206.

[moo] If t>t1 at step 208, then the system proceeds to step 216 to determine if t>t2. It can additionally be seen by reference to FIGS. 9 and 10 that the system will alternatively proceed from step 214 to step 216 to determine if t>t2.

If t≤t2 at step 216, then the system computes the projected G'(x, y, t) using T'(x, y, t−1) at step 218, which is saved in memory 206. The system then proceeds to compute the difference between G(x, y, t) and G'(x, y, t) as E(x, y, t) at step 220. At this point the system uses the Least Square Model Fitting (LSM) algorithm to fit the E(x, y, t) within the mesh window of [x−9 . . . x+9, y−9 . . . y+9] mesh grids at step 222 and proceeds back to step 210 to calculate the DIFF(x, y, t) from G(x, y, t) and G(x, y, t−1).

If t>t2 at step 216, then the system uses G(x, y, t−1) and T'(x, y, t−1) and E(x, y, t−1) to plot the 3D surface as G(x, y, t)=G(x, y, t−1) * T'(x, y, t−1)+E(x, y, t−1) at the view port at step 224, which is then sent to display 226.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A balloon catheter comprising:
a catheter and a balloon attached to said catheter;
a mesh affixed to said balloon, said mesh having:
members extending longitudinally and circumferentially about the balloon into columns and rows respectively, each member of said mesh having a resistance or impedance and each member of said mesh is configured to change in resistance or impedance as the member is deformed such that, when the member comprises a length (L) a measured resistance or impedance will be different than when the member comprise a length ($L_1$) where $L_1$ is greater than L;
wherein the columns and rows intersect each other at nodes and a change in resistance or impedance between each node may be determined.

2. The balloon catheter according to claim 1 wherein said nodes comprise knots.

3. The balloon catheter according to claim 1 further comprising an integrated circuit having pins connected to ends of the columns and rows.

4. The balloon catheter according to claim 3 wherein said integrated circuit is molded into a tube, which is affixed to said catheter.

5. The balloon catheter according to claim 4 wherein said integrated circuit includes flexible connection leads that extend out through the tube and connect to the ends of the columns and rows.

6. The balloon catheter according to claim 4 wherein said integrated circuit comprises holes such that a balloon inflation medium may pass there through.

7. The balloon catheter according to claim 4 further comprising a computer coupled to said integrated circuit, wherein said integrated circuit comprises a timing controller and a driver, said timing controller is coupled to said driver and said driver is coupled to at least one member, and said timing controller processes commands from said computer and provides timing information to said driver to activate the at least one member.

8. The balloon catheter according to claim 7 wherein said integrated circuit further comprises an analog to digital converter and a serializer, wherein said serializer is coupled to said timing controller and said analog to digital converter is coupled to said serializer, said analog to digital converter converting a received analog signal to a digital signal and said serializer sending the digital signal to said timing control in a serial fashion.

9. The balloon catheter according to claim 1 wherein the balloon is selected from a material selected from the group consisting of: latex, a thermoplastic elastomeric material, silicon, polyurethane and combinations thereof.

10. The balloon catheter according to claim 1 wherein said mesh is affixed to an outer surface of said balloon.

11. The balloon catheter according to claim 1 wherein said mesh is integrally formed with said balloon.

12. The balloon catheter according to claim 1 wherein resistance or impedance of a member is correlated to a change in length (ΔL) of the member as follows:

$$R=f(\Delta L),$$

where R is resistance or impedance.

13. The balloon catheter according to claim 1 wherein each member comprises a radio-opaque material.

14. A method for constructing the balloon catheter of claim 1 comprising the steps of:
   forming the mesh by extending the members longitudinally and circumferentially to form the columns and rows; and
   affixing the mesh to the balloon.

15. The method according to claim 14 wherein the step of forming a mesh further comprising forming a grid such that the columns and rows contact each other at nodes and a change in resistance or impedance between each node may be determined.

16. The method according to claim 15 wherein the nodes are formed as knots.

17. The method according to claim 16 further comprising the step of connecting ends of the columns and rows to pins of an integrated circuit.

18. The method according to claim 17 further comprising the step of molding the integrated circuit into a tube, to be affixed to a catheter.

19. The method according to claim 18 wherein the integrated circuit includes flexible connection leads that extend out through the tube and the method further comprises the step of connecting the ends of the columns and rows to the flexible connection leads.

20. The method according to claim 18 further comprising the step of forming holes in the integrated circuit such that a balloon inflation lumen can pass there through.

21. The method according to claim 14 further comprising the step of affixing the mesh to an outer surface of the balloon.

22. The method according to claim 14 further comprising the step of integrally forming the mesh with the balloon.

23. The method according to claim 14 further comprising the step of correlating a change in length (ΔL) of a member to a measured change in resistance or impedance of the member by using the formula:

$$R=f(\Delta L),$$

where R is resistance or impedance.

\* \* \* \* \*